(12) United States Patent
Feng et al.

(10) Patent No.: US 8,714,001 B2
(45) Date of Patent: May 6, 2014

(54) FLOATING MECHANISM LOADING VEHICLE PROVIDED WITH DOUBLE SHAFTS AND EIGHT WHEELS FOR PAVEMENT ACCELERATED LOADING TEST

(75) Inventors: Jinxiang Feng, Jinan (CN); Xingyu Guo, Jinan (CN); Ying Han, Jinan (CN); Qingzhen Wu, Jinan (CN); Xuguang Wang, Jinan (CN); Peng Zhang, Jinan (CN); Xiangzhen Kong, Jinan (CN); Zhiguang Guan, Jinan (CN); Xianggui Li, Jinan (CN); Qian Jia, Jinan (CN); Jiwei Zhang, Jinan (CN); Huijun Wang, Jinan (CN)

(73) Assignee: Shandong Jiaotong University, Jinan (CN)

( * ) Notice: Subject to any disclaimer, the term of this patent is extended or adjusted under 35 U.S.C. 154(b) by 317 days.

(21) Appl. No.: 13/389,694

(22) PCT Filed: May 31, 2010

(86) PCT No.: PCT/CN2010/073382
§ 371 (c)(1),
(2), (4) Date: Feb. 9, 2012

(87) PCT Pub. No.: WO2011/017963
PCT Pub. Date: Feb. 17, 2011

(65) Prior Publication Data
US 2012/0137762 A1    Jun. 7, 2012

(30) Foreign Application Priority Data
Aug. 10, 2009 (CN) ...................... 2009 2 0031278 U

(51) Int. Cl.
*G01M 17/02*    (2006.01)
(52) U.S. Cl.
USPC ......................................................... 73/146

(58) Field of Classification Search
None
See application file for complete search history.

(56) References Cited

U.S. PATENT DOCUMENTS 5,861,552 A * 1/1999 Clayton et al. ............. 73/116.06
2009/0064793 A1 3/2009 DiMartino et al.

FOREIGN PATENT DOCUMENTS

| CN | 101240523 A | 8/2008 |
| CN | 101644647 PX | 2/2010 |
| CN | 102607974 A * | 7/2012 |
| RU | 2148691C1 A | 5/2000 |
| SU | 1079731 A1 | 3/1984 |

OTHER PUBLICATIONS

Xiao, Junheng et al.; The Development of Mobile Load Test Car for Dynamic Track Inspection; Chinese Railways; Dec. 2008; No. 12; pp. 16-19.

* cited by examiner

*Primary Examiner* — Lisa Caputo
*Assistant Examiner* — Jermaine Jenkins
(74) *Attorney, Agent, or Firm* — Michael J. Donohue; Davis Wright Tremaine LLP

(57) ABSTRACT

Disclosed is a floating mechanism loading vehicle provided with double shafts and eight wheels for pavement accelerated loading test. The floating mechanism loading vehicle comprises front and rear rotating shafts (5), on each of which two loading steel wheels (3) and two backhaul steel wheels (2) are mounted, the loading steel wheels (3) being fixed on the rotating shafts (5) and the backhaul steel wheels (2) being rotatable round the rotating shafts (5). During the loading rolling course, the loading steel wheels (3) runs on the loading rail (4), while during the unloading backhaul course, the backhaul steel wheels (2) runs on the backhaul rail (1).

3 Claims, 2 Drawing Sheets

FLOATING MECHANISM LOADING VEHICLE PROVIDED WITH DOUBLE SHAFTS AND EIGHT WHEELS FOR PAVEMENT ACCELERATED LOADING TEST

CROSS-REFERENCE TO RELATED APPLICATION

This application claims the benefit of Chinese Patent Application No. 2009 2003 1278.X filed on Aug. 10, 2009 in the State Intellectual Property Office of China, the disclosure of which is incorporated herein by reference.

BACKGROUND OF THE INVENTION

1. Field of Invention

The present invention relates to the apparatus for testing the material and fabric of the pavement, more particularly, to a pavement accelerated loading testing apparatus.

2. Description of the Related Art

A pavement accelerated loading testing apparatus is a special apparatus for testing the material and fabric of the pavement. In current pavement accelerated loading testing apparatus, the loading steel wheels and the backhaul steel wheels are fixed on different rotating shafts, as shown in FIGS. 3, 4, which illustrate a conventional loading truck. Since the loading steel wheels 3 and the backhaul steel wheels 2 of the loading vehicle of the conventional pavement accelerated loading testing apparatus are fixed at different rotating shafts, the loading rail represents a special curve and the distance between the loading rail and the backhaul rail are varied, which affects the stability and safety of the apparatus and requires a complicated machining and assembling process, which in turn causes difficulty in maintenance.

SUMMARY OF INVENTION

The present invention has been made to overcome or alleviate at least one aspect of the above mentioned disadvantages. Accordingly, an object of present invention is to provide a loading vehicle with a greater safety, reliability and stability, furthermore, the manufacturing and assembling process of the loading vehicle is simplified which achieves a cost reduction.

According to an aspect of the present invention, there is provided a floating mechanism loading vehicle provided with double shafts and eight wheels for pavement accelerated loading test, which comprises front and rear rotating shafts, on each of which two loading steel wheels and two backhaul steel wheels are mounted, the loading steel wheels being fixed on the rotating shafts and the backhaul steel wheels being rotatable round the rotating shafts.

During the loading rolling course, the electromotor reducer assembly drives the front driving wheel to rotate, the double-acting oil cylinder forces the longitudinal girder to move downward and the supporting frame to move upward, so the free end of the longitudinal girder moves downward about the traction shaft and thus drives the balance shaft to move downward. Through the balance girder, the load is uniformly applied to the front driving wheel and the rear driven wheel. The loading steel wheels and the loading rail applied the needed load to the pavement via the front driving wheels and the rear driven wheels, so that the front driving wheels and the rear driven wheels perform the loading rolling course, the backhaul steel wheels do not contact with the backhaul rail during the loading rolling course.

During the unloading backhaul course, the double-acting oil cylinder forces the supporting frame to move downward and the longitudinal girder to move upward, so the longitudinal girder moves upward about the traction shaft and thus drive the balance shaft to move upward. The front driving wheel and the rear driven wheel are lifted by the balance girder to leave the pavement. Thus a unloading backhaul movement is performed under the action of the self-guided backhaul steel wheels and a backhaul force, the loading steel wheels do not contact with the loading rail during the unloading backhaul course.

REFERENCE NUMERALS

Figure 1:
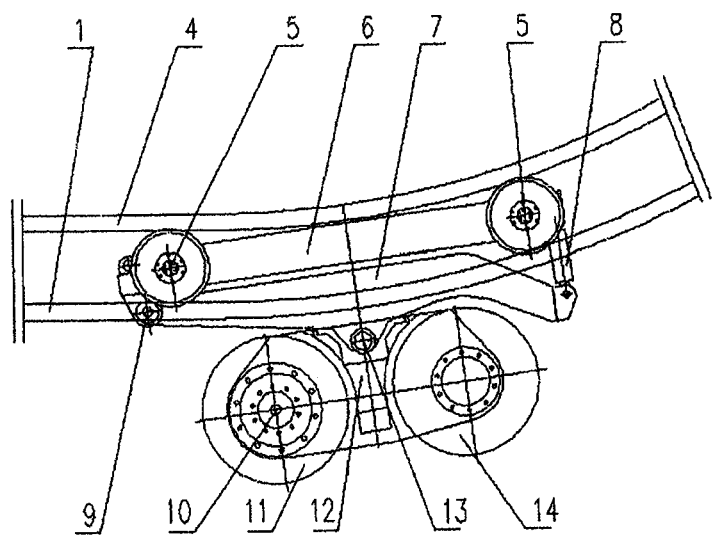
FIG. 1, FIG. 2 are a front view and left view of a floating mechanism loading vehicle provided with double shafts and eight wheels for pavement accelerated loading test according to present invention.

1—backhaul rail
2—backhaul steel wheel
3—loading steel wheel
4—loading rail
5—rotating shaft
6—supporting frame
7—longitudinal girder
8—double-acting oil cylinder
9—traction shaft
10—electromotor reducer assembly
11—front driving wheel
12—balance girder
13—balance shaft
14—rear driven wheel

DETAILED DESCRIPTION OF PREFERRED EMBODIMENTS

Preferred embodiments of the present invention will be described hereinafter in detail with reference to the attached drawings, wherein the like reference numerals refer to the like elements throughout the specification. These embodiments should not be construed as being limited to the embodiment set forth herein, rather for illustrative purpose.

Figure 2:
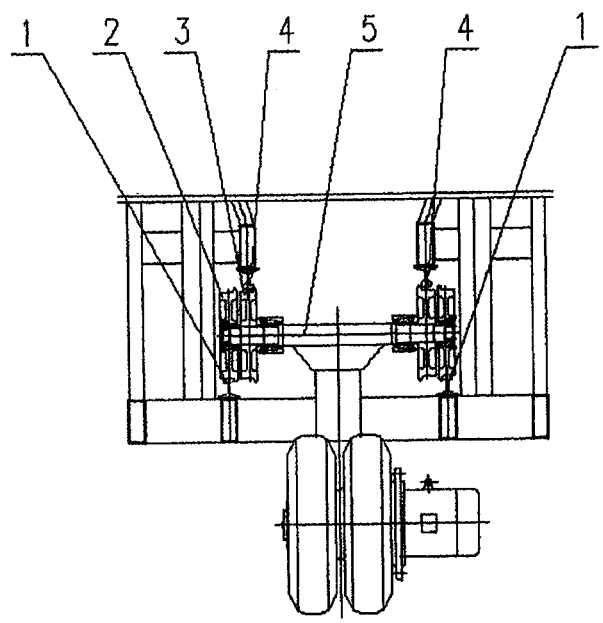
Figure 3:
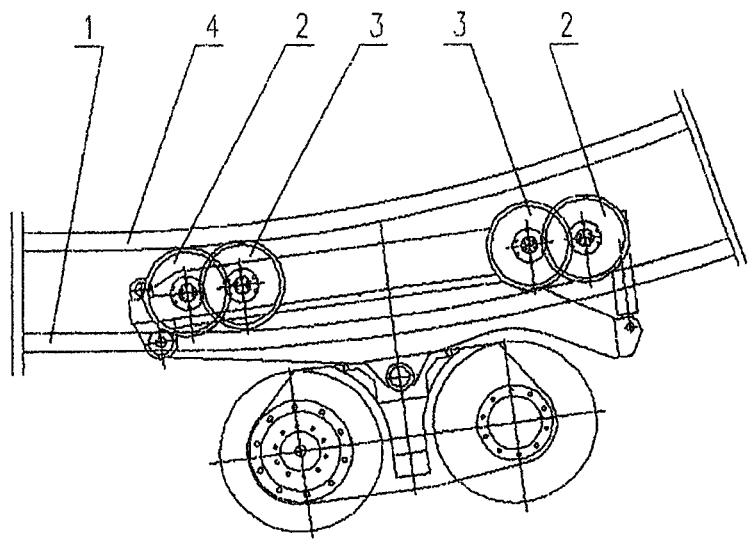
FIG. 3, FIG. 4 are a front view and left view of a floating mechanism loading vehicle provided with four shafts and eight wheels for pavement accelerated loading test according to present invention.
Figure 4:
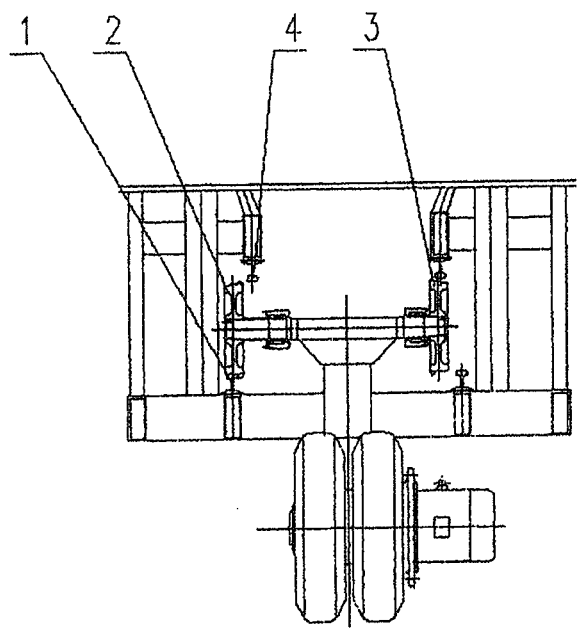

Referring to FIGS. 1-2, a floating mechanism loading vehicle for pavement accelerated loading test according to present invention comprises a backhaul rail 1, backhaul steel wheels 2, loading steel wheels 3, a loading rail 4, rotating shaft 5, a supporting frame 6, a longitudinal girder 7, a double-acting oil cylinder 8, a traction shaft 9, an electromotor reducer assembly 10, a front driving wheel 11, a balance girder 12, a balance shaft 13 and a rear driven wheel 14.

The loading vehicle is provided with a front rotating shaft and a rear rotating shaft, two backhaul steel wheels 2 and two loading steel wheels 3 are mounted on each rotating shaft 5. The loading steel wheels 3 are fixed on the rotating shaft 5 and the backhaul steel wheels 2 are rotatable round the rotating shaft 5.

The double-acting oil cylinder 8 is fixed at the right end of the supporting frame 6, the traction shaft 9 is fixed at the left end of the supporting frame 6. The longitudinal girder 7 represents a flatwise S shape, with its right end connecting with the double-acting oil cylinder 8 and its left end connecting with the traction shaft 9. The middle portion of the longitudinal girder 7 connects with the balance shaft 13 whose lower end connects with a rolling assembly.

The rolling assembly consists of the front driving wheel 11, the electromotor reducer assembly 10, the rear driven wheel 14 and the balance girder 12. The electromotor reducer assembly 10 connects with the wheel shaft of the front driving wheel 11, the wheel shaft of the front driving wheel 11 connects with the wheel shaft of the rear driven wheel 14 through the balance girder 12, and the balance shaft 13 connects with the balance girder 12 and the longitudinal girder 7.

During the loading rolling course, the electromotor reducer assembly 10 drives the front driving wheel 11 to rotate, the double-acting oil cylinder 8 pushes the longitudinal girder 7 to move downward and the supporting frame 6 to move upward, so the free end of the longitudinal girder 7 move downward about the traction shaft 9 and thus drives the balance shaft 13 to move downward. Through the balance girder 12, the load is uniformly applied to the front driving wheel 11 and the rear driven wheel 14. The loading steel wheels 3 and the loading rail 4 apply the needed load to the pavement via the front driving wheel 11 and the rear driven wheel 14, so that the front driving wheel 11 and the rear driven wheel 14 perform the loading rolling course, the backhaul steel wheels 2 do not contact with the backhaul rail 1 during the loading rolling course.

During the unloading backhaul course, the double-acting oil cylinder 8 pulls the supporting frame 6 to move downward and the longitudinal girder 7 to move upward, so the longitudinal girder 7 move upward about the draught shaft 9 and thus drive the balance shaft 13 to move upward. The front driving wheel 11 and the rear driven wheel 14 are lifted by the balance girder 12 to leave the pavement. Thus an unloading backhaul movement is performed under the action of the self-guided backhaul steel wheels 2 and a backhaul force, the loading steel wheels 3 do not contact with the loading rail 4 during the unloading backhaul course.

When the loading vehicle performs the loading rolling operation, the four loading steel wheels 3 mounted on the front and rear shafts run along the loading rail 4. While performing the unloading backhaul operation, the four backhaul steel wheel 2 mounted on the front and rear shafts run along the backhaul rail 1.

The loading vehicle can be manufactured according to the drawings. For the purpose of clarity, other well known features involved in present invention are omitted.

Although several exemplary embodiments have been shown and described, it would be appreciated by those skilled in the art that various changes or modifications may be made in these embodiments without departing from the principles and spirit of the disclosure, the scope of which is defined in the appended claims and their equivalents.

The invention claimed is:

1. A floating mechanism loading vehicle provided with double shafts and eight wheels for pavement accelerated loading test, comprising
   front and rear rotating shafts (5), on each of which two loading steel wheels (3) and two backhaul steel wheels (2) are mounted, the loading steel wheels (3) being fixed on the rotating shafts (5) and the backhaul steel wheels (2) being rotatable round the rotating shafts (5).

2. The floating mechanism loading vehicle for pavement accelerated loading test according to claim 1, further comprising:
   a loading rail, on which the loading steel wheels run during a loading rolling course;
   a backhaul rail, on which the backhaul steel wheels run during an unloading backhaul course.

3. The floating mechanism loading vehicle for pavement accelerated loading test according to claim 1, wherein
   during loading rolling course, the loading steel wheels and the loading rail apply a load onto the pavement through a front driving wheel and a rear driven wheel, so that the front driving wheel and the rear driven wheel perform the loading rolling course, the backhaul steel wheels do not contact with the backhaul rail during the loading rolling course;
   during unloading backhaul course, the front driving wheel and the rear driven wheel lift up and leave the pavement, so that an unloading backhaul movement is performed under the action of the self-guided backhaul steel wheel and a backhaul force, the loading steel wheels do not contact with the loading rail during the unloading backhaul course.

* * * * *